(12) United States Patent
Poteet et al.

(10) Patent No.: US 7,154,102 B2
(45) Date of Patent: Dec. 26, 2006

(54) SYSTEM AND METHODS FOR DETECTION AND IDENTIFICATION OF CHEMICAL SUBSTANCES

(75) Inventors: Wade Martin Poteet, Tucson, AZ (US); Laurence Marsteller, Tuscon, AZ (US); Timothy D. Shriver, Vail, AZ (US)

(73) Assignee: CDEX, Inc., Rockville, MD (US)

( * ) Notice: Subject to any disclaimer, the term of this patent is extended or adjusted under 35 U.S.C. 154(b) by 16 days.

(21) Appl. No.: 10/784,889

(22) Filed: Feb. 24, 2004

(65) Prior Publication Data

US 2005/0077476 A1 Apr. 14, 2005

Related U.S. Application Data

(63) Continuation-in-part of application No. 10/717,921, filed on Nov. 21, 2003.

(60) Provisional application No. 60/449,834, filed on Feb. 27, 2003, provisional application No. 60/448,864, filed on Feb. 24, 2003, provisional application No. 60/427,935, filed on Nov. 21, 2002.

(51) Int. Cl.
*G01J 1/42* (2006.01)
(52) U.S. Cl. .................................. 250/372
(58) Field of Classification Search ................. 250/372
See application file for complete search history.

(56) References Cited

U.S. PATENT DOCUMENTS

| | | | |
|---|---|---|---|
| 4,897,551 A | 1/1990 | Gersh et al. | 250/461.1 |
| 4,977,325 A | 12/1990 | Bowen et al. | 250/461.2 |
| 5,157,261 A | 10/1992 | Grey et al. | 250/458.1 |
| 5,281,826 A | 1/1994 | Ivancic et al. | 250/461.1 |
| 5,306,642 A | 4/1994 | Reagen et al. | 436/106 |
| 5,424,959 A | 6/1995 | Reyes et al. | 364/498 |
| 5,760,898 A | 6/1998 | Haley et al. | 356/318 |
| 5,912,466 A | 6/1999 | Funsten et al. | 250/372 |
| 5,937,026 A | 8/1999 | Satoh | 378/44 |
| 6,178,227 B1 | 1/2001 | Sato | 378/117 |
| 6,263,291 B1 | 7/2001 | Shakespeare et al. | 702/85 |
| 6,266,390 B1 | 7/2001 | Sommer, Jr. et al. | 378/45 |
| 6,459,767 B1 | 10/2002 | Boyer | 378/121 |

(Continued)

FOREIGN PATENT DOCUMENTS

EP 0806652 A2 11/1997

(Continued)

OTHER PUBLICATIONS

International Search Report dated Feb. 8, 2005.

(Continued)

*Primary Examiner*—David Porta
*Assistant Examiner*—Mindy Vu
(74) *Attorney, Agent, or Firm*—Hogan & Hartson LLP

(57) ABSTRACT

The invention provides a system and method utilizing, among other things, fluorescence spectroscopy in the ultraviolet portion of the electromagnetic spectrum to determine chemical species and concentrations. The basic measuring system includes optics, a spectrograph, a detector, and an energy source ("head" components), along with a computer and control electronics and power source capable of generating and detecting unique fluorescence signatures for individual and unique mixtures of chemical substances including, for example, prescribed and/or compounded medications, alcohol products, food types, synthetic drugs, narcotics, perfumes, liquids, and the like.

14 Claims, 18 Drawing Sheets

U.S. PATENT DOCUMENTS

| | | |
|---|---|---|
| 6,490,030 B1 | 12/2002 | Gill et al. ............. 356/71 |
| 6,501,825 B1 | 12/2002 | Kaiser et al. ............. 378/45 |
| 6,505,059 B1 * | 1/2003 | Kollias et al. ............. 600/316 |
| 6,519,315 B1 | 2/2003 | Sommer, Jr. et al. ......... 378/45 |
| 6,771,369 B1 | 8/2004 | Rzasa et al. ............. 356/326 |
| 6,868,344 B1 | 3/2005 | Nelson ............. 702/31 |
| 6,903,817 B1 | 6/2005 | Sarger et al. ............. 356/318 |
| 7,006,214 B1 | 2/2006 | Rzasa et al. ............. 356/300 |
| 2003/0160231 A1 | 8/2003 | Cole et al. ............. 257/22 |
| 2004/0007665 A1 | 1/2004 | DiFoggio et al. ......... 250/269.1 |
| 2004/0063214 A1 | 4/2004 | Berlin et al. ............. 436/94 |
| 2004/0085535 A1 | 5/2004 | Hammer et al. ............. 356/330 |
| 2005/0134836 A1 | 6/2005 | Paldus et al. ............. 356/73 |
| 2005/0248758 A1 | 11/2005 | Carron et al. ............. 356/301 |

FOREIGN PATENT DOCUMENTS

| | | |
|---|---|---|
| EP | 0806652 A3 | 4/1998 |
| EP | 1220165 A2 | 7/2002 |
| EP | 1220165 A3 | 3/2004 |
| GB | 2 365 966 A | 2/2002 |
| WO | WO 02/16917 A1 | 2/2002 |
| WO | WO 02/097407 A1 | 12/2002 |

OTHER PUBLICATIONS

International Search Report for PCT/US 03/37292 dated Apr. 23, 2004.

International Search Report for PCT/US2004/005320 dated Feb. 8, 2005.

International Search Report for PCT/US2003/00259 dated Apr. 10, 2003.

\* cited by examiner

SYSTEM AND METHODS FOR DETECTION AND IDENTIFICATION OF CHEMICAL SUBSTANCES

CROSS REFERENCE TO RELATED APPLICATIONS

This application is a Continuation-in-Part (CIP) of U.S. patent application Ser. No. 10/717,921 filed Nov. 21, 2003 which claims priority under 35 U.S.C. § 119(e) to U.S. Provisional Patent Application No. 60/427,935 filed Nov. 21, 2002. This application also claims priority under 35 U.S.C. § 119(e) to U.S. Provisional Patent Application Nos. 60/448,864 (filed on Feb. 24, 2003) and Pat. Ser. No. 60/449,834 (filed on Feb. 27, 2003), the disclosures of which are incorporated by reference in their entirety herein.

BACKGROUND OF THE INVENTION

1. Field of the Invention

The invention relates generally to the field of substance and material detection, inspection, and classification, and more particularly to an electronic scanning detection system (e.g., a fluorescence spectrograph) with a high degree of specificity and accuracy, operating in the ultraviolet portion of the electromagnetic spectrum which is used to identify specific individual and unique mixtures of substances including, for example, medications and alcohol products.

2. Discussion of the Related Art

Ultraviolet ("UV") fluorescence spectroscopy is an analytical technique used to identify and characterize chemical and biological materials and compositions. In operation, UV fluorescence systems direct energy (in the form of concentrated photons) from an excitation source toward a target area using, for example, reflective and/or refractive optics. Photoelectric interactions of the photons with the sample material produce detectable wavelength-shifted emissions that are typically at longer wavelengths (toward the visible) than the absorbed excitation ultraviolet photons.

The wavelength shift is due to an energy transfer from the incident photons (at an appropriate wavelength) to the target materials. The transferred energy causes some of the sample's electrons to either break free or enter an excited (i.e., higher) energy state. Thus, these excited electrons occupy unique energy environments that differ for each particular molecular species being examined. As a result, electrons from higher energy orbital states "drop down" and fill orbitals vacated by the excited electrons. The energy lost by the electrons going from higher energy states to lower energy states results in an emission spectra unique to each substance. When this process occurs in a short time, usually 100 nanoseconds or less, the resultant photon flux is referred to as fluorescence.

The resultant emission spectrum generated is detected with an ultraviolet spectrograph, digitized and analyzed (i.e., wavelength discrimination). Each different substance within the target area produces a unique spectrum that can be sorted and stored for comparison during subsequent analyses of known or unknown materials.

UV fluorescence spectroscopy does have some drawbacks. First, it can be affected by interference (or clutter). Interference is defined as unwanted UV flux reaching the detector that does not contribute directly to the identification of a material of interest. For example, when attempting to detect illegal substance on clothing, clutter can arise from exciting unimportant molecules in the target area, exciting materials close to the detector/emitter region, external flux from outside the target area (including external light sources) and scattering from air and/or dust in the light path. Thus, one goal of the invention is enabling efficient and accurate discrimination between all these and other sources of interference in conjunction with an appropriate analysis system (using specific algorithms and spectral filtering).

UV fluorescence systems are also limited in terms of sensitivity distances. Greater distances between the substance of interest and the UV excitation source and detector result in weaker return photon flux (i.e., weaker, if any, fluorescence) from the sample material. Factors influencing the range and sensitivity include integration time, receiving optics aperture, source power and the characteristics of the path through which the ultraviolet light travels.

Conventional spectroscopy and detection techniques include, among other things, neutron activation analysis, ultraviolet absorption, ion mobility spectroscopy, scattering analysis, nuclear resonance fluorescence, quadrupole resonance and various chemical sensors. Each of these methodologies, however, suffers from deficiencies. For example, neutron activation analyses, while capable of directly measuring ratios of atomic constituents (e.g., hydrogen, oxygen, nitrogen, and carbon) require large energy sources (such as accelerators) that have high power demands. Traditional UV absorption and scattering techniques are subject to high degrees of inaccuracy (i.e., false alarms and omissions) absent sizeable reference resources and effective predictive analysis system. Scattering analysis techniques suffer similar shortcomings.

Ion mobility spectroscopy devices are currently in use at many airports for "wiping" analysis, but suffer from low sensitivities and have high maintenance demands. Resonance fluorescence is an emerging and promising technology, but requires a large, complex energy source for operation. Quadrupole resonance techniques offer a good balance of portability and accuracy, but are only effective for a limited number of materials (i.e., they have an extremely small range of materials they can reliably and accurately detect). Finally, chemical sensors, while very accurate, are slow acting and have limited ranges. Furthermore, chemical sensors do not always produce consistent results under varying environmental conditions (e.g., high humidity and modest air currents).

SUMMARY OF THE INVENTION

The invention relates to a system and methods for material detection, inspection, and classification. In particular, the invention includes an electronic scanning detection system (e.g., a fluorescence spectrograph) with a high degree of specificity and accuracy, operating in the ultraviolet portion of the electromagnetic spectrum used to identify specific individual and unique mixtures of substances (including remote, real-time measurements of individual chemical species in complex mixtures). The substances can include prescribed and/or compounded medications and/or alcohol products. Alternatively, the substances may be food types, synthetic drugs, narcotics, perfumes, liquids, and the like.

Nearly 95% of all drugs prescriptions are directed to a discreet group of approximately 200 individual drugs. Within that group of 200 drugs, there are about 30 medications that are considered "bad actors" resulting in adverse drug events ("ADEs") if administered in combination with other medications (e.g., nitro medications and Viagra®). In some instances, these interactions can be lethal or have other significant medical consequences.

In particular, adverse drug interactions occur in about 6.5% of all drug administrations at hospitals resulting in approximately 3,000–7,000 annual deaths (and translating into about $5.6 million in additional costs at an average size teaching hospital). Such events can be, and often are, the result of inadvertent medication errors. These errors include medicating at the wrong time, omissions or unauthorized additions of medications and/or incorrect dosages. Other medications errors include medicating the wrong patient or failures to properly document and administrations. Finally, errors can be attributed to counterfeiting by substitution and/or dilution of constituent drug ingredients during administrations or during the disposal of narcotics.

Conventional methodologies for dispensing medications typically follow a one-way procedure. First, a medical professional prescribes the medication. That prescription is then communicated to a pharmacy that dispenses the medication either directly to the patient, or to a hospital that then receives the prescribed medication. A medical professional, such as a nurse, then matches the medication to the patient based up a patient's medical chart. Thus, after a medication is initially dispensed from a pharmacy or other distribution point there is little, if any, mechanism that verifies it to be the correct drug immediately prior to being administered to the patient. After administration little more is done other than to record that the drug has been given to the patient. Thus, traditional dispensing systems rely on "tagging" procedures to identify/verify medications and/or chemicals.

Quality control and assurance protocols at manufacturing facilities are similarly deficient. Traditionally, drug/chemical quality is evaluated by obtaining select samples of individual pills or doses at some point after production. Individual samples are sacrificed for quality control testing and the results are extrapolated to the entire batch. Consequently, a significant portion of every batch of manufactured medications is never subjected to direct quality control testing (for purity or dosage) prior to being administered. The invention remedies many of these shortcomings.

There are established software applications that can evaluate the potential interactions between known medications. There is, however, no measured in $m^2$ technology available enabling a caregiver to efficiently identify unlabeled medications (and/or to evaluate potential interactions between several unidentified medications).

The invention provides a system and method for identifying medications and other chemicals (e.g., alcohol products) during each step of the manufacturing and administration process. In particular, the invention enables identification and verification of chemical species by obtaining and evaluating chemical spectral signatures to provide real time validation of solid and liquid chemicals. The invention provides verification that the measured constituents of chemical compositions (e.g., medications) have not been intentionally or otherwise substituted or diluted, thereby substantially reducing the potential for, among other things, undetected errors in medication selection, mislabeling, administration, inadvertent substitution and/or purposeful counterfeiting.

The invention is designed to be deployed anywhere in the manufacturing and distribution channel of chemical materials to validate quality, including checkpoints, warehouses, hospitals and pharmacies, and to provide a final check before passing medications over the counter to the consumer. In one embodiment, the invention can be designed to be mobile, battery operated and/or be configured to require little or no operator interpretation of the results. For example, the invention can be used to monitor the quality of medications received, mixed or maintained at a hospital's central pharmacy (or a compounding pharmacy). Thereafter, the system and method can track the movement of a medication throughout a hospital until it arrives at, and is administered to, the patient.

Similarly, the system and method can correlate medication administration information (e.g., time and dosage) by reading a patients bar-coded name bracelet (or other patient identification information such as an eye scan, thumb print, etc). The invention is generally non-invasive and can be configured to directly evaluate chemicals or drugs through clear bubble wrap packaging or, in the case of liquids, while in a syringe or vial. Alternatively, the invention can be used when placed in direct contact with a chemical substance. Thus, the invention can minimize the distribution, sale or use of counterfeit drugs or chemicals (whether by means of look-a-like drugs and/or deceptive packaging).

The invention is also applicable in other situations. For example, the system can provide a non-invasive means for directly measuring and identifying chemicals and drugs (or containers suspected of containing such materials) at ports of entry or during routines law enforcement activities. Similarly, the invention can be used a local pharmacies to verify the quality of prepared and individually formulated medications and is also applicable to home health care uses whereby the patient can validate their own medications prior to use.

More specifically, the invention enables a hospital (or manufacturer) to track a chemical or drug as it moves through the hospital (or manufacturing facility) and before it is given to a patient. The invention obtains a signature scan for a chemical or drug (or mixtures thereof) and rapidly and accurately compares them to known or predetermined chemical signatures. Thus, the invention provides a closed loop, real-time, feedback system that repeatedly compares and verifies the identity and quality of chemical substances (e.g., compares the spectra of the medication or substance under consideration to a known or evolving library of spectral images.

The invention can include any known scanning device or combinations thereof Computer and control electronics can also be connected to or used in tandem with the invention. In one embodiment, the invention may include an optical scanning device, a spectrograph, a detector, and an energy source. In another embodiment, the invention may include a scanning device that may be portable and/or that has no input keyboard or monitor screen. In this embodiment, the scanning detection device communicates using an input spectrograph and an output of a series of lights (e.g., green, yellow, amber, red) mounted on the scanning device.

In general, the invention provides a mechanism for collecting unique "fingerprint" identifications (i.e., gathers information such that the fingerprint may be determined in a timely manner) of target materials that are used to distinguish them from other similar substances. The fingerprint may include any quantifiable characteristic(s) pertaining to the substance, such as excitation wavelengths, barcodes, electronic signatures, and the like.

The invention may also include an accessible database of known characteristic(s) pertaining to certain agents and substances. An accessible computer system or other storage means enables the time, place and type of substance administered to be documented. In one embodiment of the invention, an ultraviolet source is used to generate fluorescence within a target area causing detectable emission at UV wavelengths that can be uniquely matched to known materials.

In one embodiment of the invention, the system may be used to simultaneously evaluate a group of different pills. In this embodiment, the operator may be permitted to manipulate a combined spectrum of a group of different pills, or other chemical substances, and use the combined spectra to identify unauthorized or inappropriate variations. Such variations may include potential drug interactions, pill deletions or additions and/or quality control verifications. Spectra of individual substances may also be combined to identify specific substances such as pills.

In accordance with one embodiment of the invention, emission photons from excited chemical substances are detected with a receiver that includes optics, a spectrograph, and a detector array. The system can further include an analysis system that identifies particular substances of interest. In one embodiment, the invention preferably operates within the ultraviolet radiation wavelength range of approximately 240 nanometers to approximately 540 nanometers (though other wavelength ranges can also be used).

Multispectral excitation and/or detection is accomplished with the invention in a number of ways. Selection and control of either excitation wavelengths or detection wavelengths can be accomplished using, among other things, a pulsed power source (e.g., a sequence-pulsed laser system) in conjunction with data collection corresponding to each pulse, a spectral filter wheel(s) to select or vary different excitation or detection wavelengths and combinations thereof. The sensitivity of the invention can be further enhanced by use of a shutter system. Use of shutters minimizes extraneous light sources by selectively limiting access of extraneous light (as well as excitation and emission light) to the detector. For example, a shutter may be triggered to open within a discreet period of time in conjunction with an excitation pulse in order to limit the interference effects of extraneous light sources.

Regardless of the particular configuration, the sensitivity limits of the system may depend on any of several factors. These factors include: energy source, intensity, cross-section of photoelectric absorption, path length, detector collecting area, detector spectral resolution, detector geometrical characteristics, integration time, and detector noise limit. A number of steps have been taken to minimize the negative effects of these factors.

Thus, the invention provides a system and methods for the detection of various chemical substances, including medications, drugs, alcohols, perfumes and food products.

The invention further provides a system and methods for facilitating the validation of medications and drugs within pharmacies, health care facilities, controlled substance disposal facilities as well as law enforcement facilities and customs facilities.

The invention further provides a system and methods for compounding pharmacies to verify the accuracy of compounded medications.

The invention further provides a system and methods for verifying the purity and/or authenticity of a variety of substances, such as perfumes and alcohols.

Modifications and variations of the present invention are possible and envisioned in light of the above descriptions. It is therefore to be understood that within the scope of the attached detailed description, examples and claims, the invention may be practiced otherwise than as specifically described.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiments of the invention. This invention may, however, be embodied in many different forms and should not be construed as limited to the embodiments set forth herein. In addition, and as will be appreciated by one of skill in the art, the invention may be embodied as a product, method, system or process.

The invention relates to a system and methods for material detection, inspection, and classification. In particular, an electronic scanning detection system (e.g., a fluorescence spectrograph) with a high degree of specificity and accuracy, operating in the ultraviolet portion of the electromagnetic spectrum is used to identify specific individual and unique mixtures of substances (including remote, real-time measurements of individual chemical species in complex mixtures). Preferably, the substances identified by the invention are exposed medications or other chemical materials (e.g., consumer alcohols) that may not otherwise be labeled, are hidden within a container or that require strict quality control measures. Certain embodiments of the invention, however, can detect substances in a cup, bottle, or other container. This feature may be desirable for quality assurance programs to evaluate and monitor substances before leaving a manufacturing facility or pharmacy prior to delivery.

Figure 1:
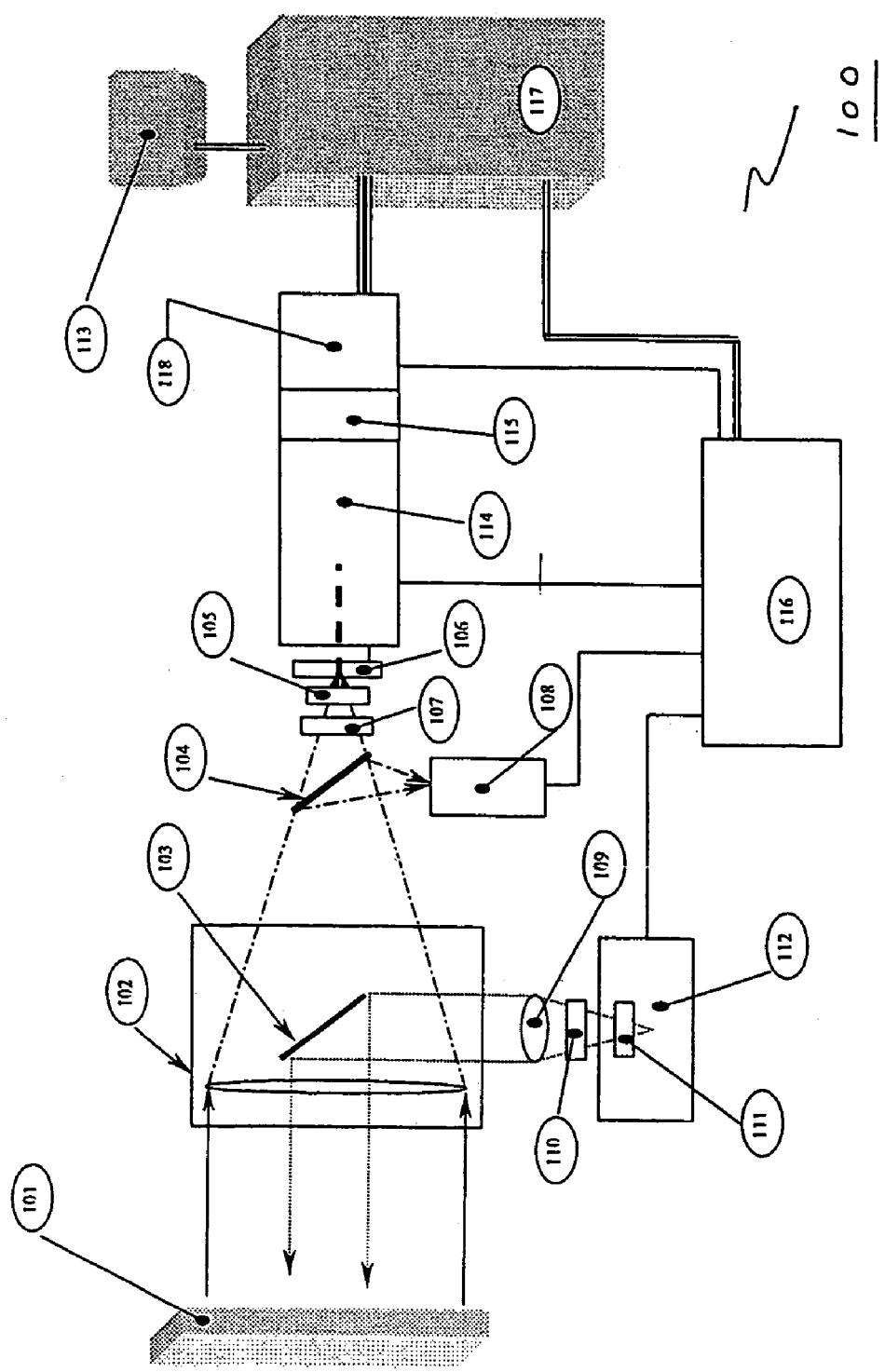
FIG. 1 illustrates a diagram of a UV absorption detection system in accordance with an embodiment of the invention.

FIG. 1 shows a diagram of a UV absorption detection system 100 in accordance with an embodiment of the invention suitable for detecting chemical substances. FIG. 1 shows the IN fluorescence detection system 100 configured for detection of various substances such as chemicals, medications, perfumes, alcohols and food products. The system may be contained in a light-tight enclosure to minimize interference from unwanted extraneous light sources during the measurement and detection process.

In FIG. 1, excitation light is generated by a source 112. The source 112 can include, among other things, a tunable laser, a flash lamp of suitable intensity, a UV LED or a solid-state UV laser diode. The excitation light may have a wide range of wavelengths and is preferable in the range of about 240 nm to 540 nm. Excitation light from the light source 112 is then passed through a spectral filter 111 (which optionally can include, among other things, a filter wheel for excitation wavelength selection), a shutter 110, and an optical lens 109. Next, a mirror 103 reflects the light toward a target area 101 (which contains the sample and species under examination). If the sample in the target area 101 photoelectrically responds to the incident excitation light (i.e. it fluoresces), the fluorescence manifests itself as a light flux within a specific band of the UV spectrum of wavelengths. Thus, the source 112, the filter 111, the shutter 110 and the optical lens 109 serve to illuminate and excite the target area 101 that may include the substance to be identified.

The UV absorption detection system 100 gathers fluorescent emissions from the sample located at the target area 101 through an input optic(s) 102. Input optic 102 can be, but is not limited to, a lightweight reflective optic(s) or an appropriate refractive (lens) optic(s). The input optic 102 in accordance with the invention can be of differing sizes depending on the desired configuration. For example, in order to detect substances at large distances, the input optic may be very large, for example 1.4 meters in diameter. On the other hand, for the input optic 102 may be significantly smaller as described below in connection with a portable detection system. In one embodiment, input optic 102 may include a handheld device or a stylus. After passing through the input optics 102, a dichroic beam splitter 104 splits the emitted light into a visible light component and a UV light component. The visible light component can optionally be directed to a camera 108 for visual target inspection and target aiming while the UV light component is directed to and through a spectrograph shutter 107, a spectral filter 105 (which optionally can include, among other things, a filter wheel for detection wavelength selection) and an input slit 106. It should be noted that shutters 110 and 107 can each be coordinated to selectively open and close to minimize interference and scatter effects from, among other things, extraneous light and dust. For example, shutters 110 and 107 can each be triggered to open within a discreet period of time in conjunction with an excitation pulse in order to limit the interference effects of extraneous light sources. Light passing through the input slit 106 enters a spectrograph 114 that is optically matched to the UV light beam.

An internal grating (not shown) inside the spectrograph 114 provides spectral separation, which involves separation of the input spectrum into its individual wavelength components. Internal optics (not shown) within the spectrograph 114 then reimage the separated input spectrum onto a CCD linear array detector 115, which may optionally be cooled. The CCD detector 115 converts the UV light components into electrical signals that are then processed by a signal processor 118 and analyzed using an attached computer 117. As will be described in greater detail below in connection with FIG. 3, the computer 117 includes an analysis system that provides for a variety of output data based on comparisons of material(s) detected within target area 101 and a database of known materials. Thus, the computer 117 executes a matching operation whereby output signals from the CCD are matched against know signature spectra of certain chemical compounds.

The data and analysis from the computer 117 are presented to a display device 113 that can include a computer monitor or a set of lights indicating the presence or absence of certain substances. A power source 116 supplies power to the various components of the UV detection system 100. The power source 116 can include, among other things, an AC main supply, batteries or similarly suitable power supplies.

Figure 2:
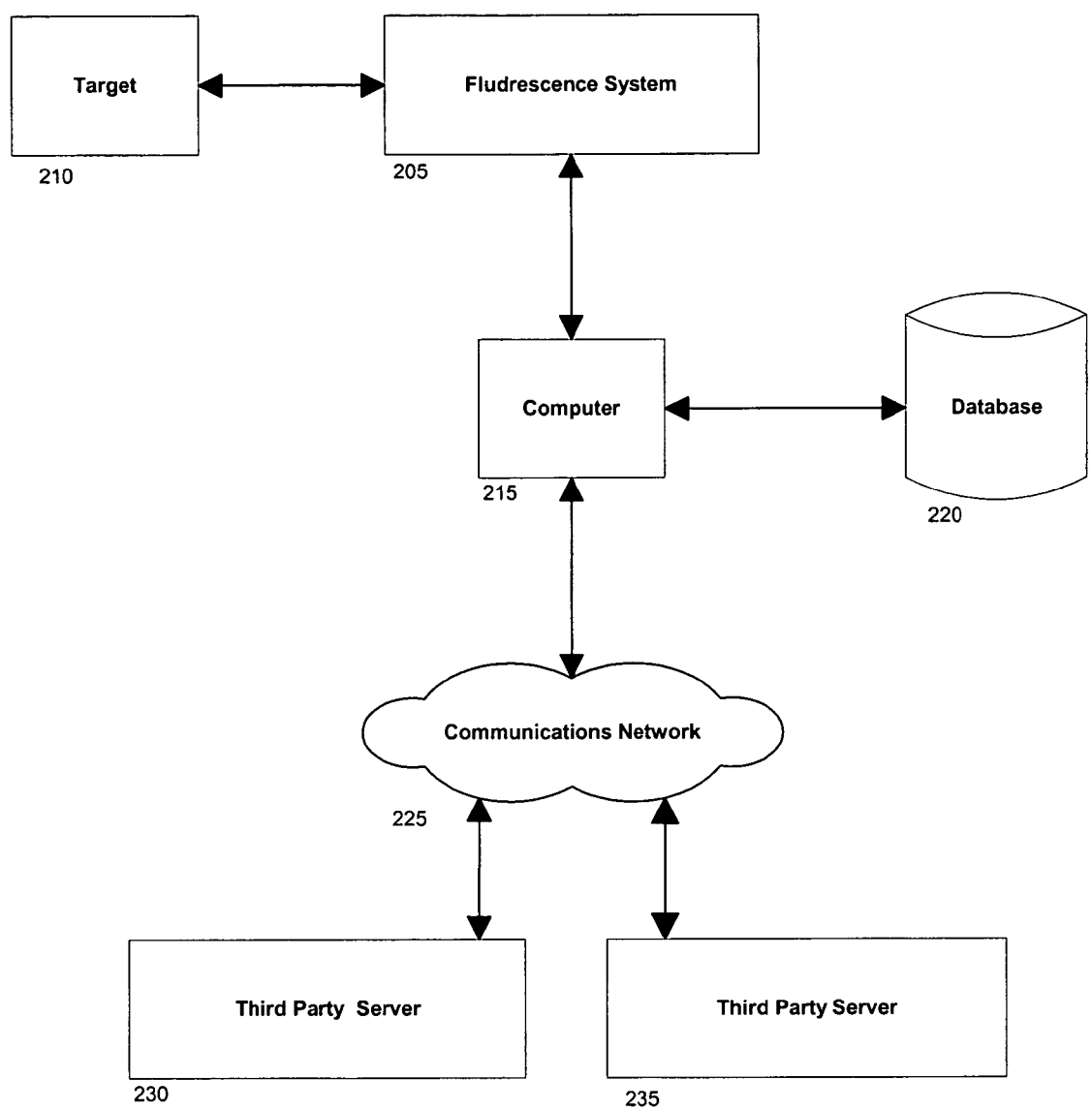
FIG. 2 illustrates a block diagram of a UV system for substance detection in accordance with an embodiment of the invention.

FIG. 2 shows a system for detecting chemical substances in accordance with an embodiment of the invention. FIG. 2 shows a fluorescence device 205, which may be similar to the system 100 of FIG. 1. FIG. 2 also shows a target 210 that is or may contain the subject to be detected. Also, in FIG. 2, a computer 215 or other processing device is coupled to the fluorescence system 205 and is capable of operating and/or receiving detected spectral data from the system 205. The computer 215 is also coupled to a database 220 which may contain spectral data for a variety of chemical substances. It is important to note that the database 220 may be integrated with in the computer 215, or may be a separate entity accessible within a computer network. In FIG. 2, the computer 215 is also coupled to third party servers 230 and 235 via a communications network 225. The communications network 225 may be any known network, such as the Internet or a local area network (LAN). It is important to note that the fluorescence system 205, computer 215 and database 220 may be integrated into a single device, such as a hand-held device, a mobile device and/or fixed mounted device.

In operation, a substance to be detected is placed onto or into the target 210. The fluorescence system 205 then obtains spectral data as described above in connection with FIG. 1. This data is then sent to the computer 215 for processing. The computer 215 then accesses the database 220 to identify the unique spectrum for each composition measured and compares it to previously generated spectra that are stored in the database 220. The computer 215 can also access third party servers 230 and 235 via the communications network 225. The third party servers 230 and 235 may be, for example pharmacy databases, hospital databases or manufacturer databases and can be accessed to learn about changes in prescriptions, changes in the compositions of substances and to monitor usage and dispensation rates for medications.

The methodology for identifying particular substances is now described in greater detail. As described above, identification of a substance includes analysis of the substance's electromagnetic spectrum. A generated spectrum can be cross-correlated and analyzed by comparison against other known reference information (e.g., other drugs or substances being administered to a patient in view of known genetic or health factors, known drug interactions and/or quality assurance information).

When evaluating a mixture of substances, for example, a pill cup with multiple medications, the mixture can be analyzed by deconvolving the spectra of the mixture into a variety of subsets. The subsets may include (1) component or individual drug signatures and/or (2) compounded spectra (of several drugs). Thereafter, the invention can determine whether the spectra of a component subset match the spectra of a known interacting drug combination. For example, the disclosed embodiments may scan a pill cup with N drugs $(D_1+D_2+\ldots D_n)$ forming a compound spectra Spectra $D_n$. Thereafter, the invention may deconvolve the spectra to, for example, (Spectra $D_1+D_2 \ldots D_{n-2}$)+(Spectra $D_{n-1}$+Spectra $D_n$), wherein (Spectra $D_{n-1}$+Spectra $D_n$) represents a potential or known negative drug interaction. The invention then signals the user that the compound spectrum (Spectra $D_n$) includes a component subset spectra for a negative drug interaction. Alternatively, the (Spectra $D_1+D_2 \ldots D_{n-2}$) may remain unidentified.

The invention may also initially identify substances, such as drugs, individually thus eliminating the need for it to deconvolve a compounded spectrum (alternatively, the invention may deconvolve a compounded spectrum to identify individual drugs). It must be recognized, however, that under certain circumstances the invention may be unable to deconvolve all possible spectra combinations for every drug combination and/or for any arbitrary amount of pills. In such instances, the invention can be configured to signal the user that not all interaction possibilities have been considered or evaluated and/or that some subsets of the total pill combination have known or potential interactions.

The output of the invention may be expressed as a probability or percentage chance of a drug interaction. The invention may include software that is either adjustable or institutionally designated (and therefore fixed) to trigger the invention's audible and/or visible drug interaction indicators (e.g., the drug interaction limits that correspond to the invention's green, yellow, amber and red lights).

The invention may further include the ability to manipulate the acquired drug spectra and/or correlate an acquired drug spectrum against a patient's known genetic or other health factors.

In accordance with an embodiment of the invention, the unique spectral signatures and subsets are assigned name and type strings (thus allowing easy discreet comparisons of each signature). Each signature can also be assigned a base point for use as a reference point along with a variable number of other points defining its characteristic spectrum.

Signatures for known compounds and mixtures may be stored in a plain text files for ease of adding new, or modifying existing signatures. As stored, the individual UV spectra of the compounds comprise an array of counts recorded in an ordered set of channels (i.e., the UV spectrum of an individual chemical or chemical mixture is a series of numbers). During initialization, the system loads the stored plain-text sample signatures into an array. The elements of the array are then compared against the evolving spectrum as it is being acquired.

Signature matching can be accomplished using, among other things, a $20^{th}$ order power series of cosine functions for curve-matching that is rapid, and allows for flexibility. Each channel for a known UV spectrum corresponds to a partial wavelength range of the UV emission wavelengths able to be recorded in the detector. Whenever UV light of a specific frequency enters the spectrometer, it enters a corresponding channel, causing the counter for that channel to be incremented. When a scan is complete, the incremented counts for all the channels are returned as an integer array.

Once the input data is accumulated in the integer array, it is matched with a signature in a spectrum using a least-square curve-fitting routine that reduces the measured spectrum to a small set of digital numbers sufficient to describe the key information contained in the spectrum. The best fit of this curve may use up to a $24^{th}$-order equation.

The signature-matching algorithm begins by comparing the description parameters stored in the database. Each parameter is checked in sequence to see if the parameter's value is within a range corresponding to a defined UV spectrum in the database. An appropriate range can be defined as three standard deviations above and below the average channel value. Comparisons can also be made using an average channel value and/or standard deviation value for each target material contained in the database.

When all the database signatures are checked, signature(s) that fall within the defined range are classified as a match. When more than one signature material qualifies as a match, the system allows for comparison of the various possible matches with the sample material (including, among other things, overlays of the spectrum). The system also enables an IDENTIFICATION mode in which the names of all the matched materials are displayed for the users consideration as well as a VERIFICATION mode in which either or both visual and audible indications are returned for the positive and/or negative sample matches.

Figure 3:
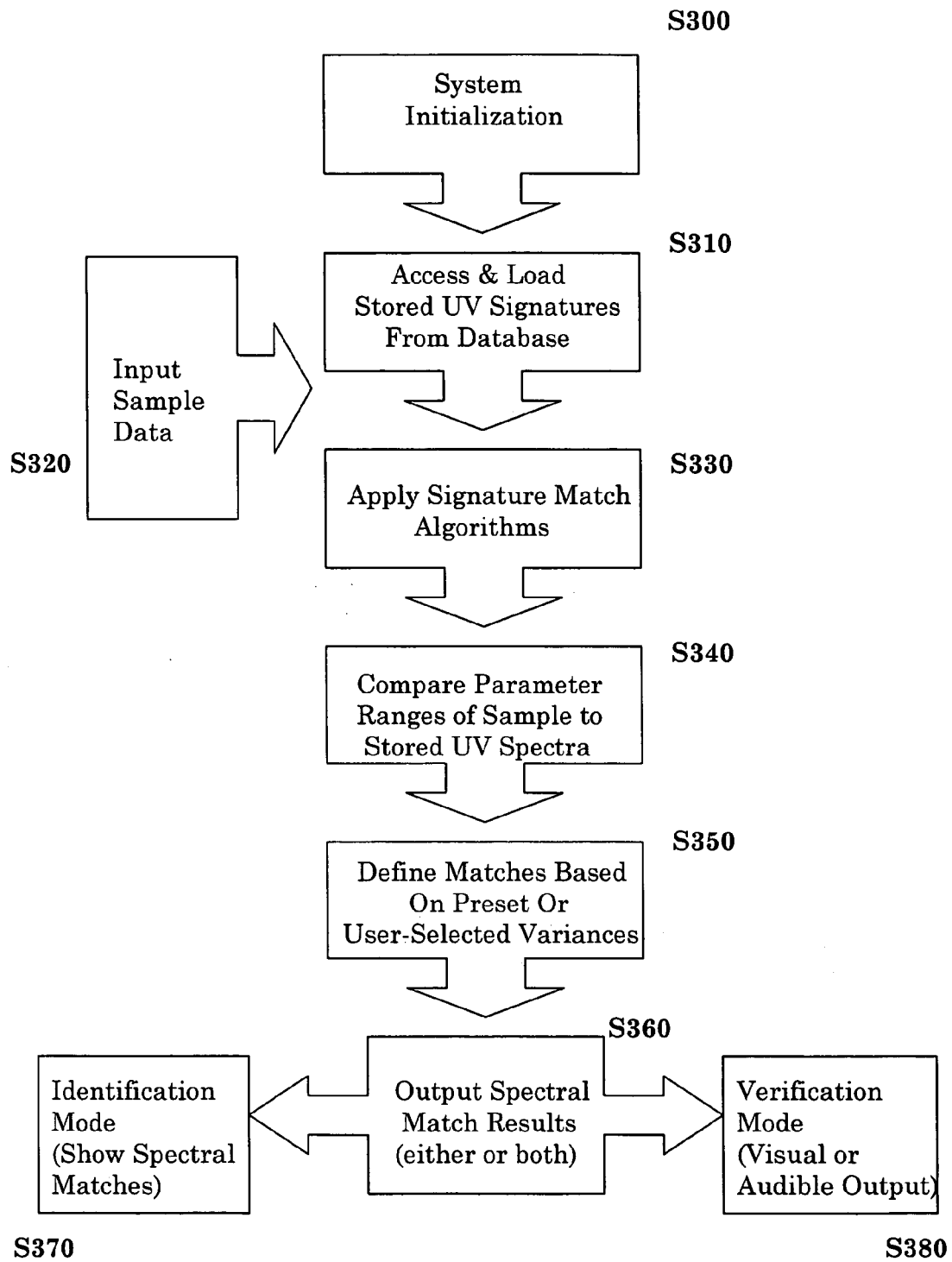
FIG. 3 is a flow chart illustrating a process for matching measured fluorescence data with known signature spectra of certain compounds in accordance with an embodiment of the invention.

FIG. 3 is a flow chart illustrating a process for matching measured fluorescence data with known signature spectra of certain compounds in accordance with an embodiment of the invention. In FIG. 3, the matching process begins at step S300 wherein the system is initialized. The process then moves to step S310 in which the system accesses and loads UV signatures from known materials that are stored on a system-accessible database. The process then moves to step S320 where the data from an evolving sample spectrum being acquired is supplied to the system. For example, this step may include illuminating the sample with UV light and receiving fluorescent light that is transmitted back from the sample. This step may also include receiving processed signals from a CCD and/or signal processor as shown in FIG. 1. In step S330 the system applies algorithms to the acquired sample data provided in step S320. This step can include, for example, application of a $20^{th}$ order power series of cosine functions for curve matching. Next, in step S340, the manipulated sample data from steps S320 and S330 is compared to the UV signatures loaded from the database in step S310. Step S340 can include, for example, using a least-square curve-fitting routine that reduces the measured spectrum to a small set of digital numbers sufficient to describe the key information contained in the spectrum, including using up to a $24^{th}$-order equation. In step S350, the system determines whether there has been a match based on the comparison procedure in step S340. A match can defined as a preset standard deviation between values from the sample spectrum and those of stored spectra, such as, for example, three standard deviations above or below a average value of a stored spectrum). Next, in step S360, the system outputs the results of any matches. Step S360 can include either (or both) of steps S370 (in which the system provides spectral results for visual inspection by the operator and/or provides overlays of the produced spectra) and step S380 (in which visual and/or audible alarms indicate a match).

Figure 4:
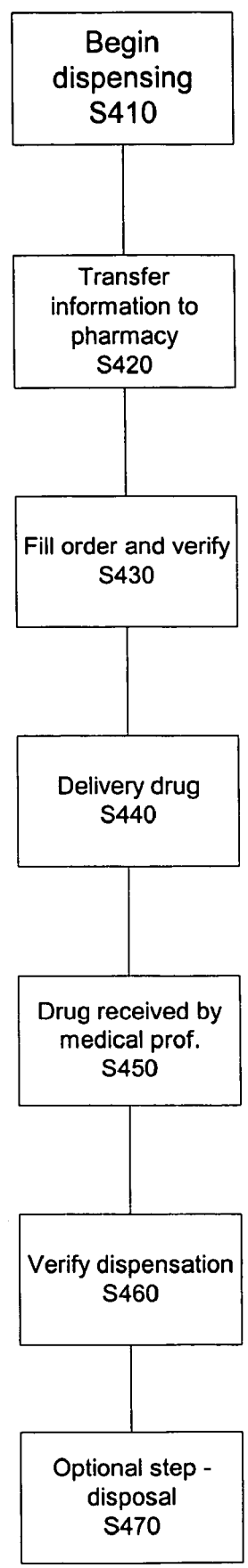
FIG. 4 illustrates a flowchart for a process for drug/medication dispensation and disposal that can be used at health care facilities in accordance with an embodiment of the invention.

FIG. 4 is a flow chart illustrating a process for drug/medication dispensation and disposal that can be used at health care facilities, including hospitals, in accordance with an embodiment of the invention. In FIG. 4, the dispensation/disposal process begins at step S410 when a treating physician prescribes a drug or other medication. The process then moves to step S420 where the information from step S410 is transmitted to a pharmacy or other initial drug distribution point. The transmission of information from a treating physician to a pharmacy in step S420 can include transmission via the Internet, by telephone, via prescription or any other method of communicating such information. Next, in step S430, the pharmacy fills the prescription. As part of the process for filling the prescription, step S430 can include verifying the medication dispensed in accordance with the process described above in FIG. 3. The process next moves to step S440 in which the drug/medication is delivered to the location at or within a healthcare facility where the drug or medication will be given to a patient. Step S440 can include storing the drug/medication until the time of administration and/or verifying the drug/medication dispensed in accordance with the process described above in FIG. 3. Next, in step S450, a nurse or other caregiver obtains or receives the drug/medication to be administered. Step S450 can include verifying the medication dispensed in accordance with the process described above in FIG. 3. The process then moves to step S460 where the drug/medication is administered to the patient. Step S460 can include verifying the medication dispensed in accordance with the process described above in FIG. 3. In particular, step S460 can include scanning the medication at the time of administration in accordance with the process described above in FIG. 3 in order to check for adverse drug interactions. Step S460 can also include, among other things, scanning a patient's identification bracelet or other personalized identifiers to track drug administration(s), to update patient records and/or to update billing and insurance information. The process can then move to step S470 in which waste materials, including in particular excess drugs/medications, are disposed. Step S470 can include verifying the drugs/medications have been properly disposed (and-not otherwise substituted or diverted) in accordance with the process described above in FIG. 3.

Figure 5:
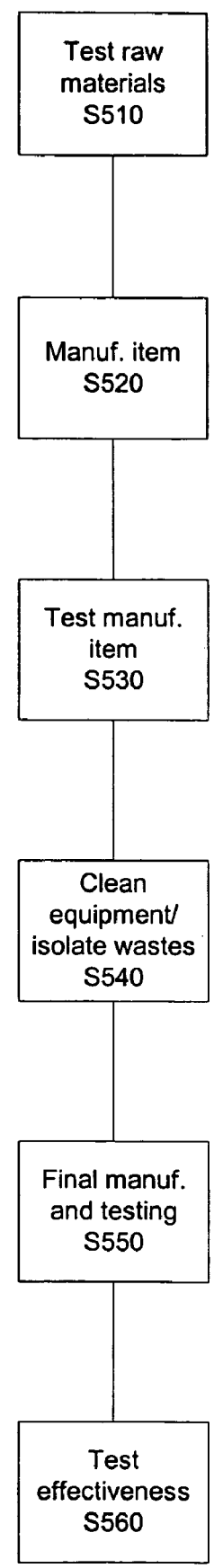
FIG. 5 illustrates a flow chart for quality control and quality analysis (QA/QC) testing at manufacturing facilities in accordance with an embodiment of the invention.

FIG. 5 is a flow chart illustrating a process for quality control and quality analysis (QA/QC) testing at chemical, drug, alcohol, perfume and other similar manufacturing facilities in accordance with an embodiment of the invention. In FIG. 5, the QA/QC process begins at step S510 in which raw materials and chemicals for the manufacturing of chemical, drugs, alcohol, drug, perfumes, etc. are tested before being used in a manufacturing process. Step S510 can include testing raw materials in accordance with the process described above in FIG. 3. The process then moves to step S520 in which the raw materials are used to manufacture the target chemical, drugs, alcohol, drug, perfume, etc. Step S520 can include testing raw materials in accordance with the process described above in FIG. 3 as each component is mixed with the others during the manufacturing process as well as testing intermediate products during the manufacturing process. Next, in step S530, the target product is tested for, among other things, purity. Step S530 can include testing for purity in accordance with the process described above in FIG. 3. Next, the process moves to step S540 in which the manufacturing equipment is cleaned and waste materials are isolated. Step S540 can include testing equipment surfaces and waste products in accordance with the process described above in FIG. 3. Thereafter, the process moves to step S550 that includes post-manufacturing procedures that can include pill formation, packaging, etc. Step S550 can include testing and verifying content in accordance with the process described above in FIG. 3. In particular, for example, the process described above in FIG. 3 can be used to verify that medications that have been packaged are properly labeled. Each of the foregoing steps can be linked to centralized database for tracking purposes, thus enabling the manufacturer to track the manufacturing process from receipt of raw materials until product shipment. Thereafter, in step S560, packaged materials can be tested to ensure they have not lost potency, been substituted, been tampered with or are forgeries. Step S560 can include testing the packaged materials in accordance with the process described above in FIG. 3.

Specific embodiments of the generalized UV absorption detection system illustrated in FIG. 1 have been used to obtain fluorescence spectra for a number of materials including a variety of pharmaceutical compositions (and dilutions thereof) as well as consumer alcohols. FIGS. 6–18 are representative of such spectra and are for illustrative purposes only and are not intended nor should they be interpreted to limit the scope of the application.

Figure 6:
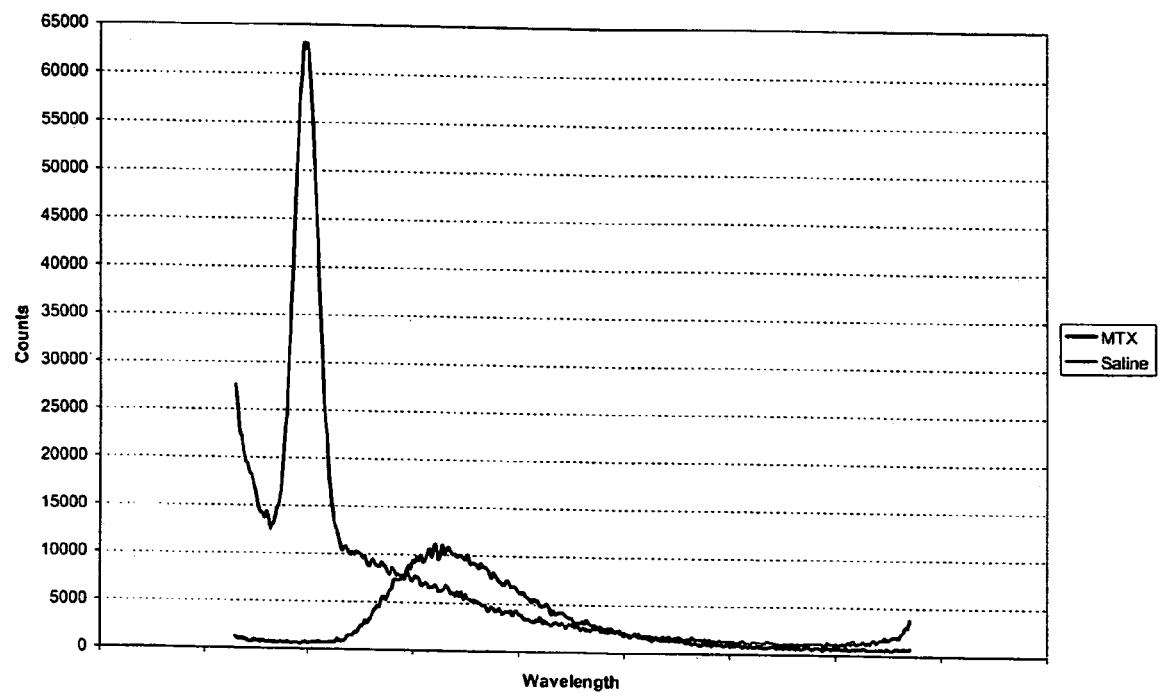
FIG. 6 illustrates the UV Spectrum of methotrexate (50 mg in 250 ml NS for IVPG) compared to normal saline as determined in accordance with an embodiment of the invention.

FIG. 6 illustrates the UV Spectrum of methotrexate (50 mg in 250 ml NS for IVPG) compared to normal saline as determined in accordance with an embodiment of the invention.

Figure 7:
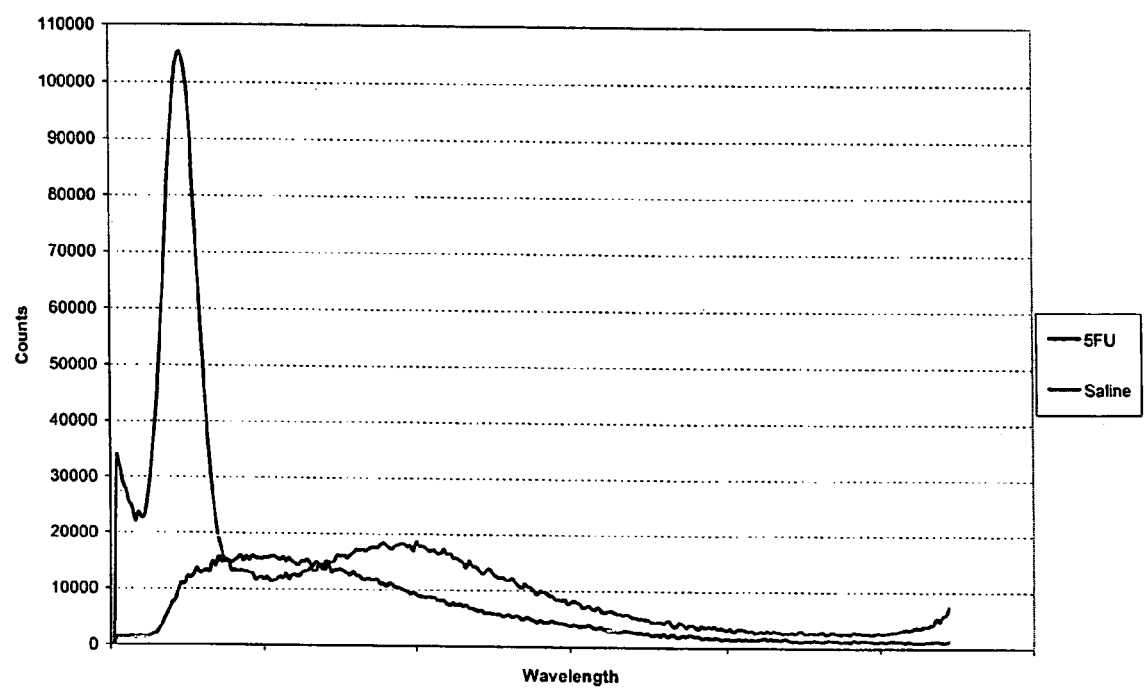
FIG. 7 illustrates the UV Spectrum of 5-fluorocil (850 mg in 50 ml NS for IVPG) compared to normal saline as determined in accordance with an embodiment of the invention.

FIG. 7 illustrates the UV Spectrum of 5-fluorocil (850 mg in 50 ml NS for IVPG) compared to normal saline as determined in accordance with an embodiment of the invention.

Figure 8:
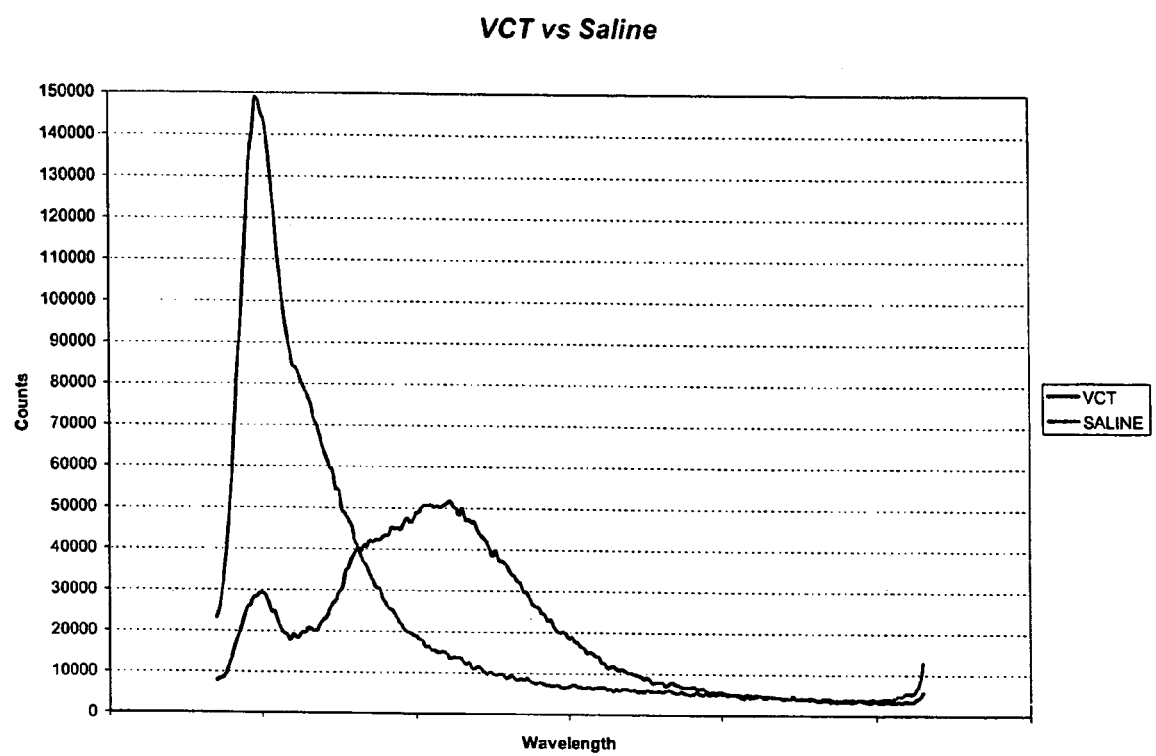
FIG. 8 illustrates the UV Spectrum of vincristine (2 mg in 50 ml NS for IVPG) compared to normal saline as determined in accordance with an embodiment of the invention.

FIG. 8 illustrates the UV Spectrum of vincristine (2 mg in 50 ml NS for IVPG) compared to normal saline as determined in accordance with an embodiment of the invention.

Figure 9:
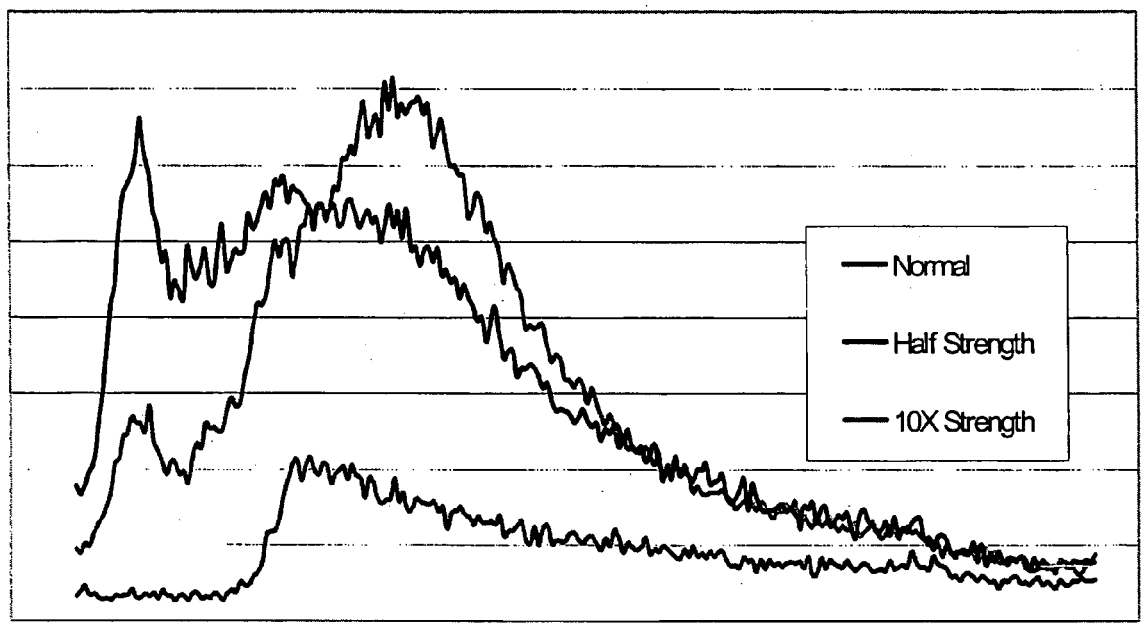
FIG. 9 illustrates the UV Spectrum of vincristrine at several different concentrations as determined in accordance with an embodiment of the invention.

FIG. 9 illustrates the UV Spectrum of vincristrine at several different concentrations as determined in accordance with an embodiment of the invention.

Figure 10:
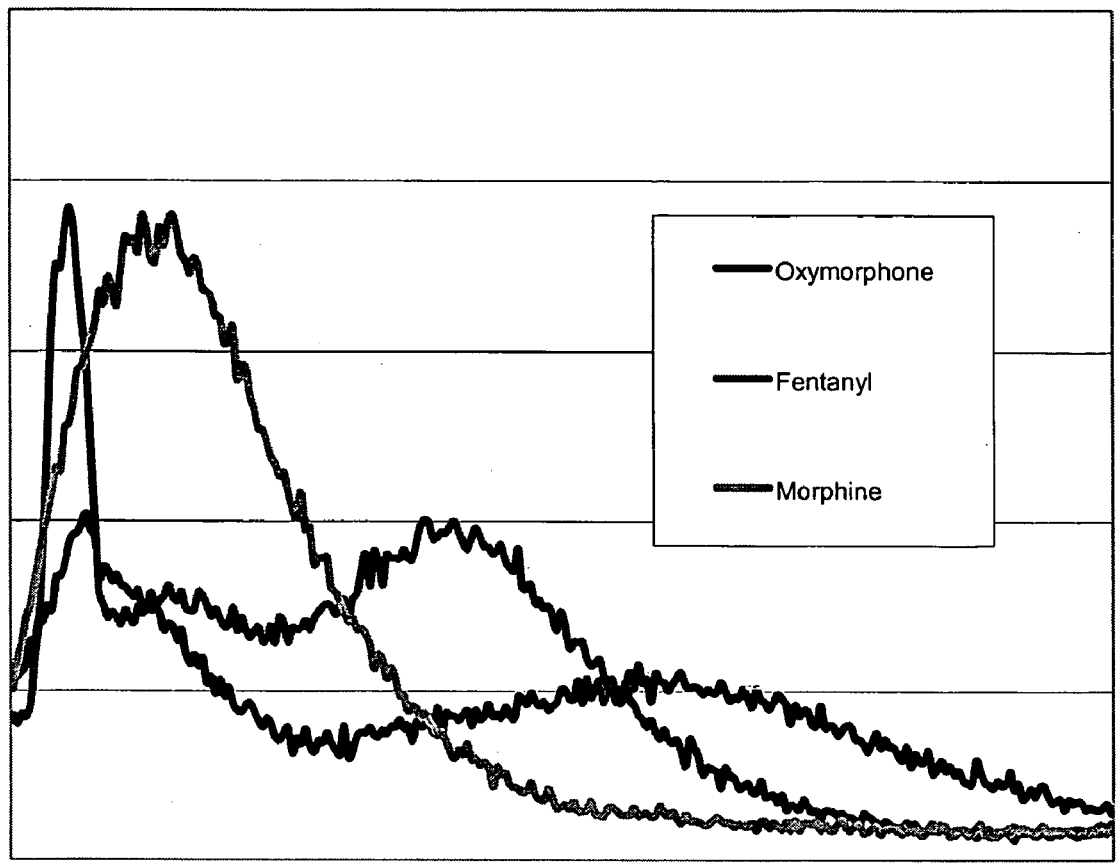
FIG. 10 illustrates the combined UV Spectrum of oxymorphone, fentanyl and morphine as determined in accordance with an embodiment of the invention.

FIG. 10 illustrates the combined UV Spectrum of oxymorphone, fentanyl and morphine as determined in accordance with an embodiment of the invention.

Figure 11:
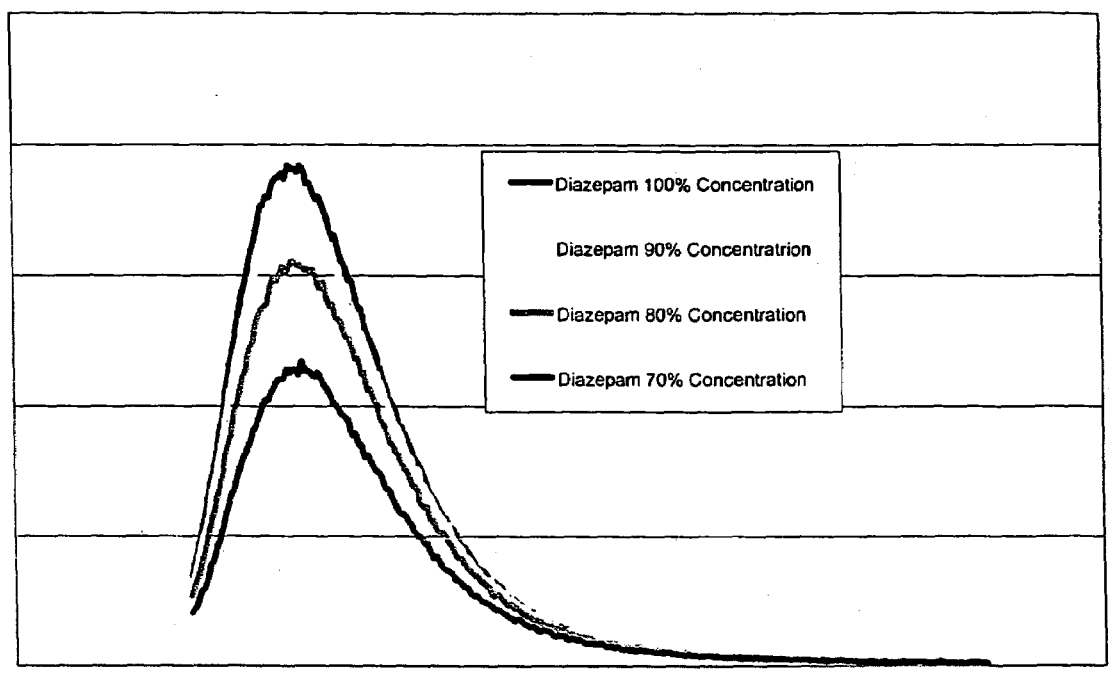
FIG. 11 illustrates the UV Spectrum of diazepam at several different concentrations as determined in accordance with an embodiment of the invention.

FIG. 11 illustrates the UV Spectrum of diazepam at several different concentrations as determined in accordance with an embodiment of the invention.

Figure 12:
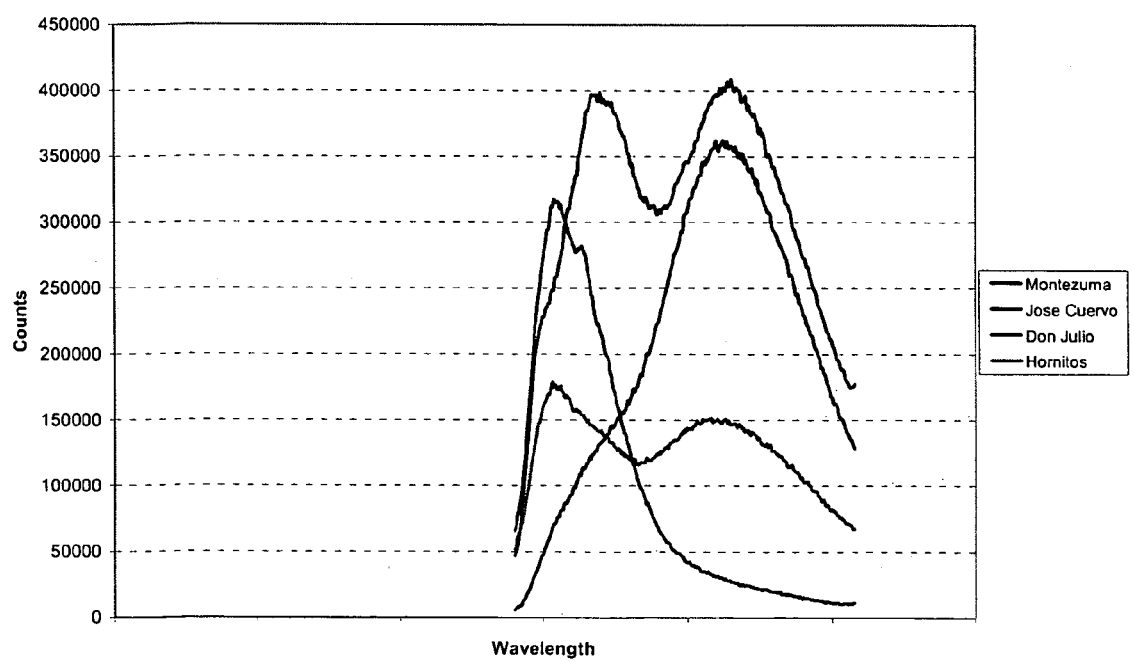
FIG. 12 illustrates the UV Spectrum of several commercially available tequilas as determined in accordance with an embodiment of the invention.

FIG. 12 illustrates the UV Spectrum of several commercially available tequilas as determined in accordance with an embodiment of the invention.

Figure 13:
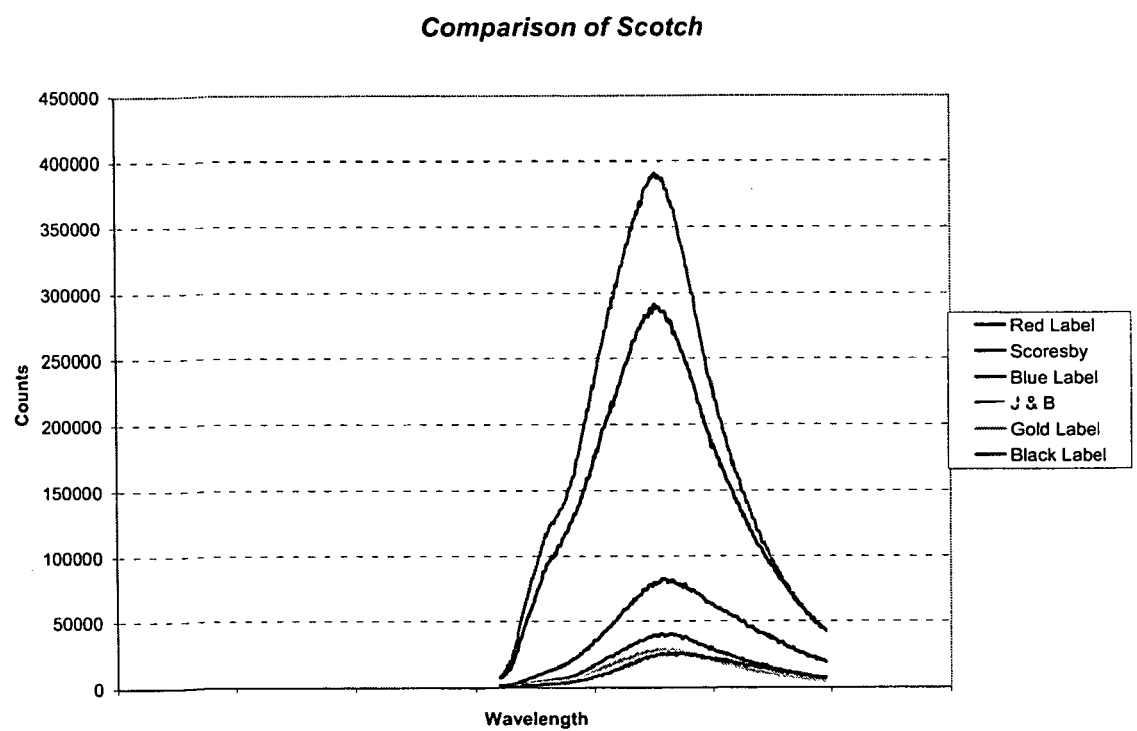
FIG. 13 illustrates the UV Spectrum of several commercially available scotches as determined in accordance with an embodiment of the invention.

FIG. 13 illustrates the UV Spectrum of several commercially available scotches as determined in accordance with an embodiment of the invention.

Figure 14:
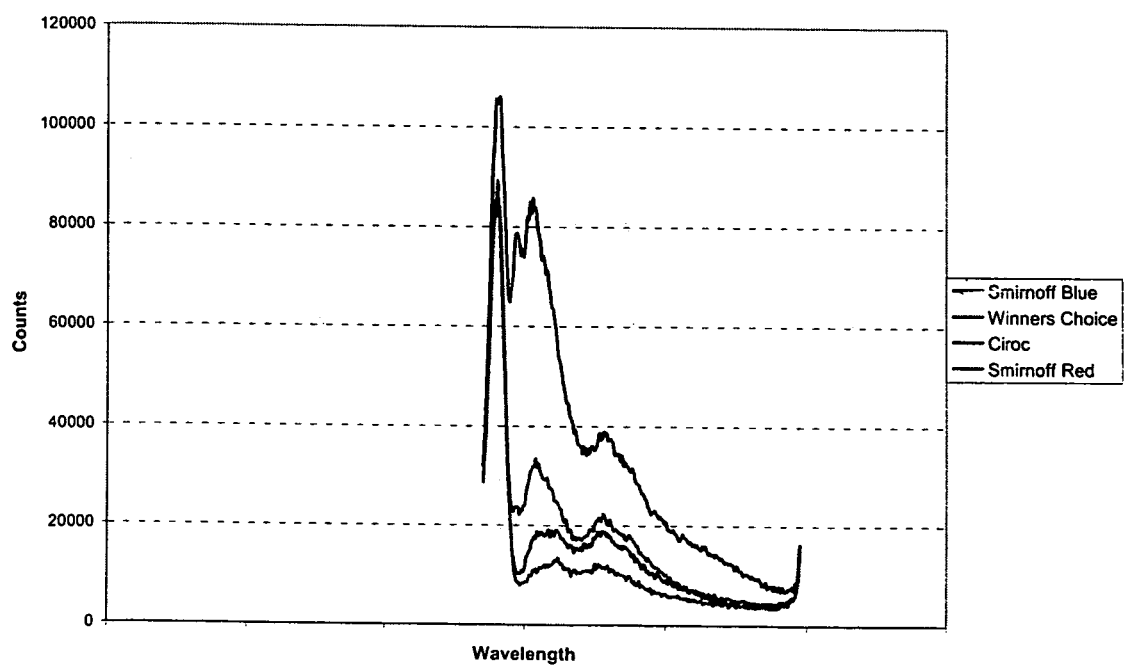
FIG. 14 illustrates the UV Spectrum of several commercially available vodkas as determined in accordance with an embodiment of the invention.

FIG. 14 illustrates the UV Spectrum of several commercially available vodkas as determined in accordance with an embodiment of the invention.

Figure 15:
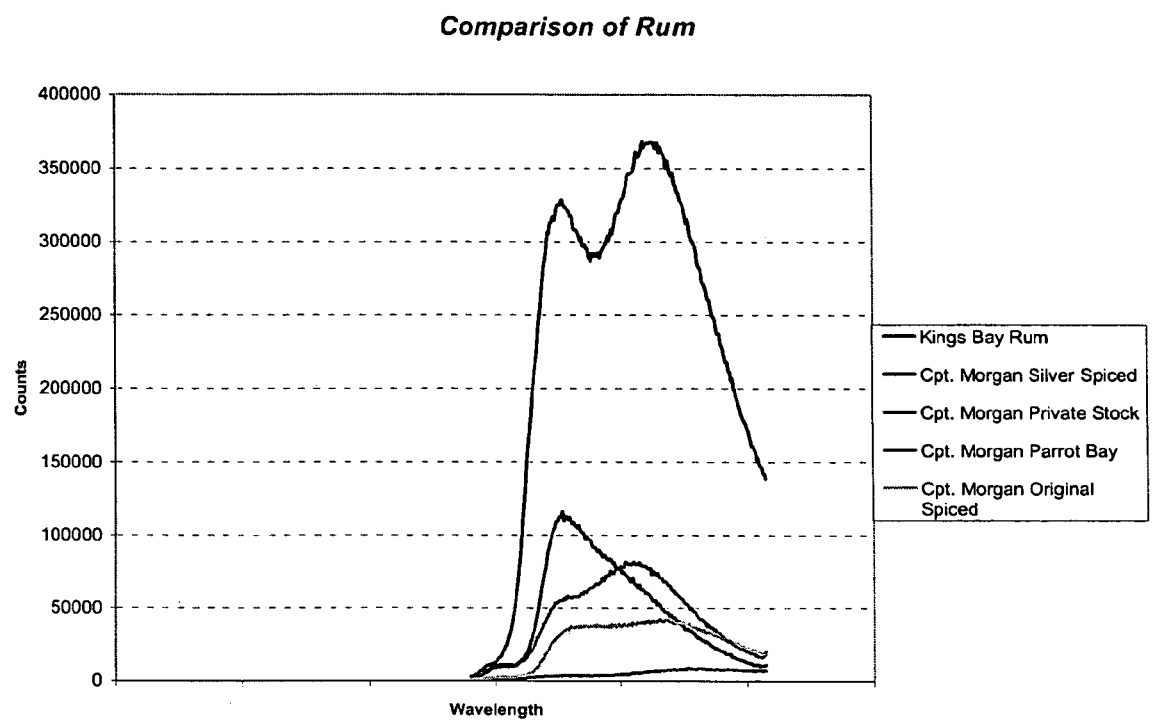
FIG. 15 illustrates the UV Spectrum of several commercially available rums as determined in accordance with an embodiment of the invention.

FIG. 15 illustrates the UV Spectrum of several commercially available rums as determined in accordance with an embodiment of the invention.

Figure 16:
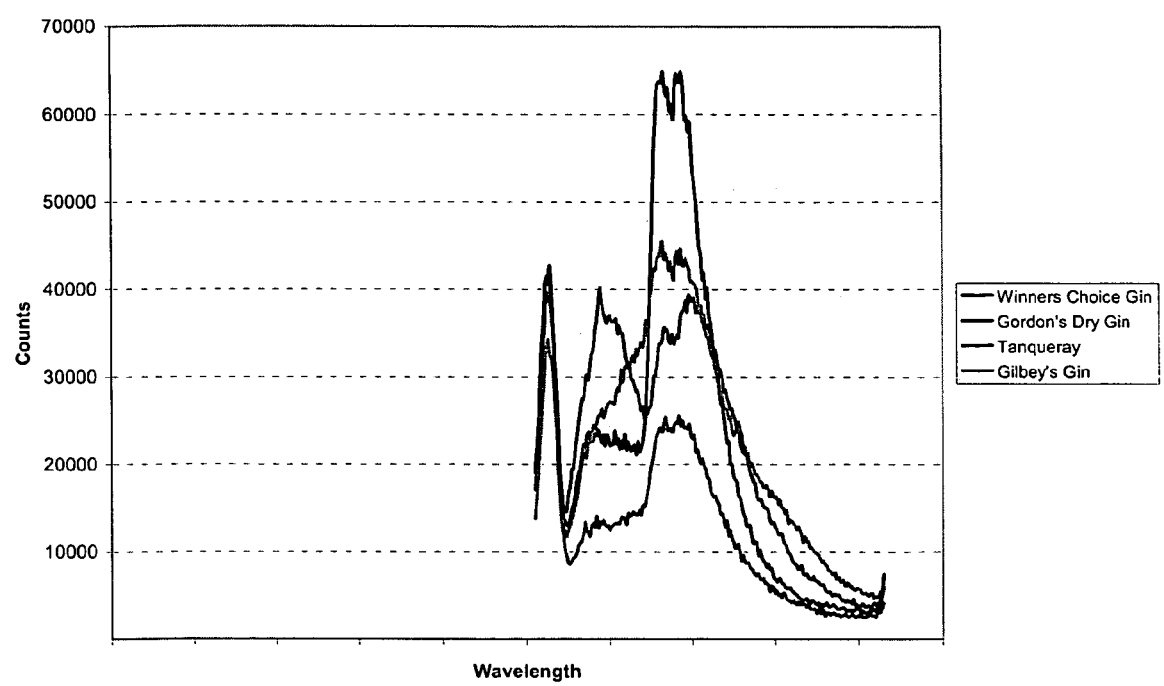
FIG. 16 illustrates the UV Spectrum of several commercially available gins as determined in accordance with an embodiment of the invention.

FIG. 16 illustrates the UV Spectrum of several commercially available gins as determined in accordance with an embodiment of the invention.

Figure 17:
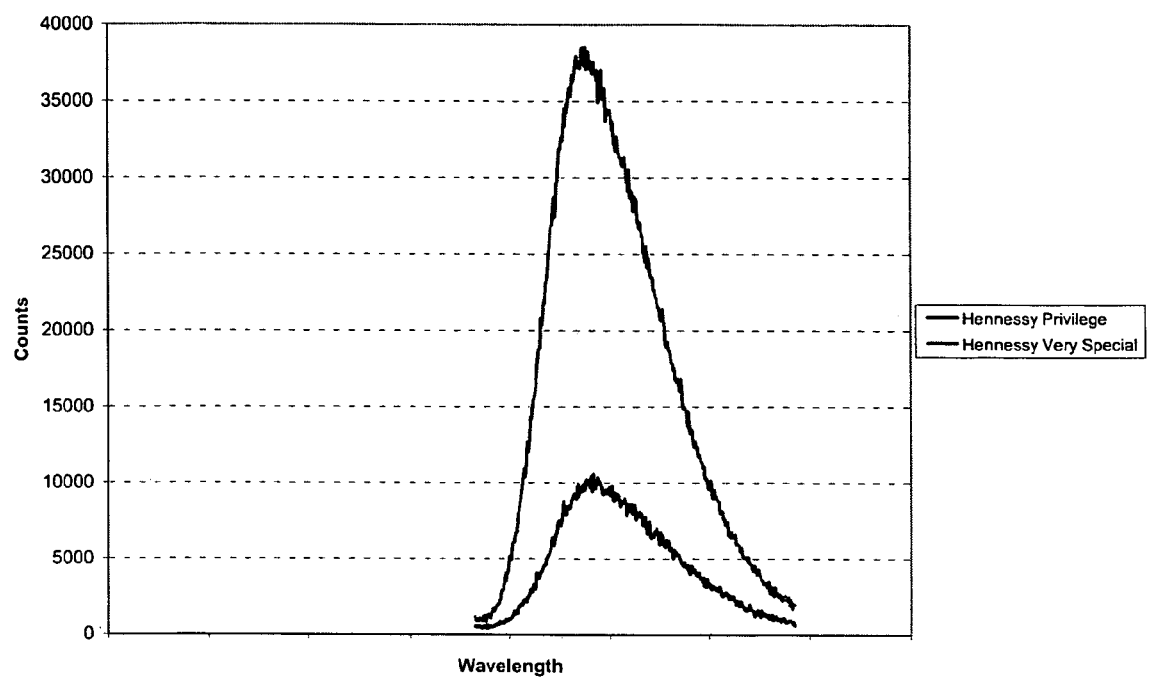
FIG. 17 illustrates the UV Spectrum of several commercially available cognacs as determined in accordance with an embodiment of the invention.

FIG. 17 illustrates the UV Spectrum of several commercially available cognacs as determined in accordance with an embodiment of the invention.

Figure 18:
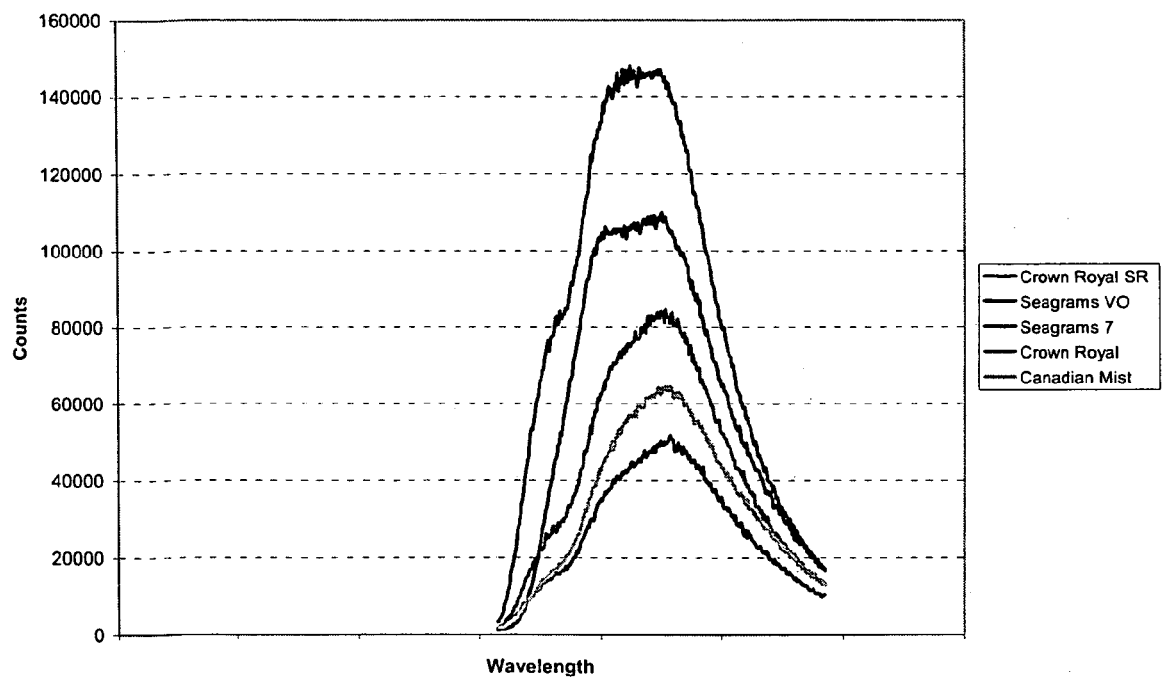
FIG. 18 illustrates the UV Spectrum of several commercially available whiskeys as determined in accordance with an embodiment of the invention.

FIG. 18 illustrates the UV Spectrum of several commercially available whiskeys as determined in accordance with an embodiment of the invention.

In one embodiment of the invention, any adverse combination of medications may cause an alarm or notice to be raised, such as the flashing of a red light. Similarly, a yellow light may be illuminated to indicate a minor interaction while a green light may indicate no drug interactions. If no alarm codes are triggered (i.e., no red or yellow lights are generated), a compounded spectrum is generated one pill at a time and the combined spectrum is stored for future reference. In this embodiment, subsequent administrations of medicine are scanned and compared to the original (stored) drug spectrum and the caregiver/operator need only simultaneously scan the combined pills prior to subsequent administrations to determine if a proper mixture of drugs is about to be administered. In the event a missing or an additional (unauthorized) drug is detected, the subsequent drug administration can be detected and flagged (i.e., identified by a red or yellow light.).

The invention has an extensive number of applications. A non-exclusive list includes, but is not limited to: any industries, processes and/or equipment requiring remote, non-invasive sensing of multiple chemical compounds or constituents (such as monitoring, commercial drug quality control and/or medication dispensing verification).

The invention can evaluate a wide range of chemical substances including, but not limited to, (a) Common toxins and/or poisons (e.g., organophosphates, acetaminophen, digoxin, warfarin, etc.); (b) Medications with narrow therapeutic window and/or low therapeutic dose to lethal dose ratios (e.g., lithium, digoxin, etc.); (c) Medications metabolized in or during the Cytochrome P450 pathway including inhibitors (e.g., cimetidine, ciprofloxin, amioderone, fluoxetine, amiodarone, clarithromycin, etc.), inducers (e.g., carbamazepine, rifampin, etc.) or other related compositions (e.g., theophylline, phenytoin, etc.); (d) Various analgesics including opioid analgesics and combinations thereof (e.g., percocet, vicodin, tylenol with codeine, etc.), muscle relaxants (e.g., corisoprodol (Soma), cyclobenzaprine (Flexeril), etc.), non-opioid analgesic combinations (e.g., fioricet, fiorinal, norgesic, etc.), nonsteroidal anti-inflamitories (e.g., ibuprofen, naproxen, etc.), opioid agonists (e.g., meperidine (Demerol), morphine, MS Contin, etc.) and related pain relievers (e.g., acetaminophen (Tylenol), tramadol (Ultram)); (e) Antipsychotics including atypical medications (e.g., clozapine (Clozaril), resperidone (Resperdal), etc.) and D2 Antagonists (e.g., haldoperidol (Haldol), chlorpromazine (Thorazine), etc.); (f) Anxiolytics/Hypnotics (e.g., benzodiazepines such as diazepam (Valium), etc.); (g) Antidepressants including heterocycluic compounds (e.g., amitriptyline (Elavil), etc.), MOA inhibitors (e.g., pheneizine (Nardil), etc.), SSRI medications (e.g., fluoxetine (Prozac), Paroxetine (Paxil), etc.) and related compositions and/or antimanic medications (e.g., bupropion (Welbutrin), etc.); (h) Bipolar agents (e.g., carbamazepine (Tegretol), Lithium, etc.); (i) Cardiovascular medications including anti-dysrhythmics (e.g., amioderone, digoxin, dofetilide (tikosyn), propafenone (Rythmol), sotalol (Betapace)), beta blockers (e.g., atenolol, caredilol, labetalol, metoprolol, propanolol), calcium channel blockers and other related compositions (e.g., diltiazem, verapamil), and diuretucs (e.g., aldactone, furosemide, HCTZ); (j) Diabetes medications and related compositions (e.g., sulfonylureas: chlorpropamide (Diabinase), glipizide, glyburide, metforman, glucovance, etc.); (k) Gastroenterological medications (e.g., antiemetics: droperidol, metoclopramide (Reglan), prochlorperazine (Compazine)); (l) Hemotology medications (e.g., warfarin, asprin) and (l) Neurological materials/Anticonvulsants (e.g., carbamasepine (Tegretol), phenobarbitol, phenytion (Dilantin), etc.); (m) Controlled Substances including Muscle Relaxants/Sedatives (e.g., chlordiasepoxide (Librium), diazepam (Valium), lorazepam (Ativan), etc.), Opioid Agonists-Antagonists (e.g., buprenorphrine (Buprenex), butorphanol (Stadol), nalbuphrine (Nubain), pentazocine (Talwin), etc.), Opioid Agonists (e.g., hydromophone (Dilaudid), meperidine (Demerol), morphine sulfate, oxymorphone (Numorphan), Anesthetics (e.g., alfentalnil (Alfenta), etomidate (Amidate), fentanyl (Sublimaze), ketamine, midazolam (Versed), propofol (Diprivan), sufentanyl (Sufenta), thiophental (Pentothal), etc.) and related compositions (e.g., phenobarbital, haloperidol, etc.).

The invention can also evaluate a wide range of consumer alcohols including, but not limited to, (a) American Whiskeys (e.g., Seagram's 7, etc.); (b) Canadian Whiskeys (e.g., Canadian Mist, Crown Royal®, Crown Royal® Special Reserve, Seagram's 7, Seagram's VO®, etc.); (c) Cognacs (e.g., Hennessy Privilege, Hennessy Very Special, etc.); (d) Gins (e.g., Gilbey's®, Gordon's®, Tanqueray®, Winner's Choice, etc.); (e) Rums (e.g., Captain Morgan Original Spiced, Captain Morgan's Parrot Bay, Captain Morgan Private Stock, Captain Morgan Silver Spiced, Kings Bay, etc.); (f) Scotches (e.g., J&B® Rare, Johnnie Walker® Red Label, Johnnie Walker® Black Label, Johnnie Walker® Gold Label, Johnnie Walker® Blue Label, Scoresby, etc.); (g) Tequilas (e.g., Jose Cuervo®, Don Julio®, Montezuma, Hornitos, etc.); (h) Vodkas (e.g., Ciroc™, Smirnoff® Red, Smirnoff® Blue, Winner's Choice, etc.).

SPECIFIC EXAMPLES

Example 1

In one embodiment, the invention may include a scanning device that can be used to scan a patient's pill cup containing a number of medications (e.g., a morning medication pill cup may include a blood pressure pill, a diabetes pill and an aspirin). In this embodiment, the invention identifies any negative or potentially adverse medication interactions or combinations. When configured in this manner, the invention can scan single or multiple pills simultaneously and thereafter generate a combined spectrum that can be marked indicating potentially adverse and/or acceptable dosing conditions. The disclosed embodiment may also (or alternatively) provide other visible or audible indications of potentially adverse and/or acceptable dosing conditions (e.g., illuminating a red light for a negative dosing condition or a green light for an acceptable dosing condition).

Example 2

In another embodiment, the invention can include a scanning device that may be configured as a portable, stand-alone device capable of testing for dangerous, irregular or unknown chemical combinations. The scanning device can optionally be configured as a self-contained scanning and diagnostic unit thus alleviating the need to be coupled to a central or remote processing or computer unit.

Example 3

In another embodiment, the invention can include a scanning device that comprises a detached, transitional product from a chemical identification system that individually identifies unknown pills contained in a mixture and provides discreet information regarding each constituent medication (e.g., linking a particular medication or pill to a particular health care facility floor with or without linking that information to a central pharmacy or a particular patient's medication list).

Example 4

In another embodiment, the invention is linked into a health care facility's billing system to update billing information after each drug administration.

Example 5

In another embodiment, the invention can be used at locations that are not linked to centralized pharmacies to detect and monitor potential drug interactions (e.g., nursing homes, adult care facilities, patient information kiosks at pharmacies or malls).

Example 6

In another embodiment of the invention, a caregiver (e.g., a nurse, a family member, the patient) can use the invention to perform a final safety test before administering a medication or mixtures thereof.

Example 7

In another embodiment of the invention, a nurse/caregiver can scan a patient's barcode or other biometric identifier (e.g., retinal scan, thumb print, etc.) to access the unique, previously determined spectra for a patient's medication or mixtures thereof. Thereafter, the spectra of a dispensed medication or mixtures can be compared to the stored spectra to ensure the proper medication or mixture is being administered. In such an embodiment, the invention can be configured to identify the person administering the medication, to identify any stray medications and provide a time/date stamp for any medication administered.

Example 8

In another embodiment, the invention can include a learning function enabling the caregiver to add new medications to the medication mixture spectra after determining there are no adverse effects.

Example 9

In another embodiment, the invention may be linked to a central pharmacy computer system that enables it to access a patient's drug list and previous medication spectra. Thereafter, the invention can calculate a combined spectrum, detect potential negative interactions and/or scan a patient's new medication mixture and assess compliance.

Example 10

In another embodiment, the invention can utilize a deconvolving computational process to assess potential drug interactions.

Example 11

In another embodiment, the invention may be utilized for treatment (i.e., medicate or identify medications) in instances where the individual under the effect of the medication is incoherent and/or otherwise unable to communicate with medical personnel (e.g., an overdose or poisoning patient).

Example 12

In another embodiment, the invention may be used in conjunction with and/or as part of a chemical (or distillery) manufacturing quality assurance and control procedure.

Example 13

In another embodiment, the invention may be used during the dispensing procedures at a pharmacy after a customer's medication bottle has been labeled, but prior to the medication being placed into the bottle. Specifically, a technician or pharmacists can quickly scan and verify a dispensed medication prior to filling a prescription. In this embodiment, the invention can also be configured to print a verified medication label and/or provide a "Re-Scan" feature to re-initiate the validation process without having to re-enter the drug information.

Example 14

In another embodiment, the invention may be used to verify that the correct chemotherapy medications (e.g., parenteral (i.e., IV) medications, narcotics, compounded drugs, antibiotics, chemotherapy drugs, etc.) are properly dispensed to a patient. In this embodiment, the invention would primarily function to reduce the rate of errors in dispensing of such medications by validating parenteral medications at both the time of admixture and also prior to administration and (2) by allowing a pharmacy technician or nurse to validate the medication administered.

Example 15

In another embodiment, the invention may be used to verify that medications such as parenteral medications (including IV and/or other compounded medications), narcotics, chemotherapy drugs, antibiotics, etc. are properly returned and/or disposed of after administration to a patient. In particular, the invention provides a hospital or care facility pharmacy an expert tool to validate the disposal of controlled medications, including those in liquid form, quantities that remain in syringes and materials that have been diluted or otherwise substituted. The invention will enable quantitative and qualitative comparisons between a medication returned for disposal with the medication initially dispensed thus helping minimize the occurrence of such medications being improperly diverted. The invention will also enable direct tracking of disposed materials by providing printed receipts and/or computer storage of disposal records.

Example 16

In another embodiment, the invention may be used for quality control and analysis testing of consumer alcohols during and after production. This embodiment can also be used to evaluate such alcohols before or after bottling. This embodiment can also be used to identify or verify the contents of unlabeled containers or as part of a procedure to identify counterfeit products. The invention can be used to evaluate alcohol products without the need to breach the container or break the container's seal.

Example 17

In another embodiment, the invention may be used to verify that correct medications, including chemotherapy drugs, antibiotics and narcotics, in various forms (e.g., pills, liquids, creams and patches) and modes of preparation (e.g.; compounded medications of all forms) are correctly dispensed to a patient. In this embodiment, the invention would primarily function to reduce the rate of errors in dispensing of such medications by validating the medications at both the time of admixture and also prior to administration.

It will be apparent to those skilled in the art that various modifications and variations can be made in the present invention and specific examples provided herein without departing from the spirit or scope of the invention. Thus, it is intended that the present invention covers the modifications and variations of this invention that come within the scope of any claims and their equivalents.

The invention claimed is:

1. A system for verifying the composition of chemical substances comprising:
   an ultraviolet fluorescence detector;
   a processor coupled to the ultraviolet fluorescence detector, the processor receiving spectral data from the ultraviolet fluorescence detector; and
   a database including predetermined signature data for a plurality of chemical substances,
   wherein the plurality of chemical substances comprises at least one of a drug, a medication, a compounded medication, a compounded chemical formulation, a controlled substance, a narcotic, an illegal drug, an alcohol, a food product and a perfume.

2. The system according to claim 1, wherein the ultraviolet fluorescence detector includes:
   an excitation light source;
   a sample receiving platform capable of receiving excitation light from said excitation light source;
   an ultraviolet light detector for receiving induced fluorescent energy; and
   an analysis module for matching said induced fluorescent ultraviolet energy against a previously determined signature spectrum.

3. The system according to claim 1, wherein the signature data includes data for at least one of a drug, a medication, a compounded medication, a compounded chemical formulation, a controlled substance, a narcotic, an illegal drug, an alcohol, a food product and a perfume.

4. A method for verifying the composition of at least one chemical substance, comprising the steps of:
   measuring induced fluorescent energy of at least one chemical substance;
   accessing a database of predetermined fluorescent signatures of chemical substances; and
   comparing the measured induced fluorescence energy of said at least one chemical substance against the predetermined fluorescent signatures of said accessed database of a plurality of chemical substances,
   wherein the plurality of chemical substances comprises at least one of a drug, a medication, a compounded medication, a compounded chemical formulation, a controlled substance, a narcotic, an illegal drug, an alcohol, a food product and a perfume.

5. The method for verifying the composition of at least one chemical substance of claim 4, wherein said step of measuring induced fluorescent energy of said at least one chemical substance includes scanning said at least one chemical substance.

6. The method for verifying the composition of at least one chemical substance of claim 4, further comprising at least one of the steps of:
   measuring said at least one chemical substance with a fluorescence inducing device;
   measuring said at least one chemical substance when said chemical substance is being manufactured;
   measuring said at least one chemical substance before said at least one chemical substance is packaged;
   measuring said at least one chemical substance after said at least one chemical substance has been packaged;
   measuring said at least one chemical substance when said at least one chemical substance is received at a distribution point;
   measuring said at least one chemical substance when said at least one chemical substance is dispensed from a distribution point;
   measuring said at least one chemical substance before said at least one chemical substance is administered;
   measuring said at least one chemical substance before said at least one chemical substance is consumed; and
   measuring said at least one chemical substance before said at least one chemical substance is disposed.

7. The method for verifying the composition of at least one chemical substance of claim 4, further comprising at least one of the steps of:
   storing said measured induced fluorescent energy of said chemical;
   updating a database;
   updating a record;
   updating a billing system;
   updating a tracking system;
   verifying the identity of said at least one chemical substance;
   verifying the purity of said at least one chemical substance;
   performing a quality control procedure;
   analyzing raw materials prior to manufacturing said at least one chemical substance;
   identifying the presence of an impurity;
   identifying an impurity;
   identifying a patient;
   identifying a patient's medication profile;
   comparing said at least one chemical substance against a patient's medication profile; and
   identifying at least one unknown chemical substance.

8. The method for verifying the composition of at least one chemical substance of claim 4, further comprising at least one of the steps of:
   alerting a user to an error;
   alerting a user to a potential chemical interaction;

alerting a user to an impurity;

alerting a user to a unmatched fluorescent signature for said at least one chemical substance; and alerting a user to an inaccurate concentration of said at least one chemical substance.

9. The method for verifying the composition of at least one chemical substance of claim 4, wherein said system is included in a quality control program.

10. The method for verifying the composition of at least one chemical substance of claim 4, wherein said system is included in a chemical substance dispensation protocol.

11. The method for verifying the composition of at least one chemical substance of claim 4, wherein said system is included in a chemical substance administration protocol.

12. The method for verifying the composition of at least one chemical substance of claim 4, wherein said system is included in a chemical substance disposal protocol.

13. The method for verifying the composition of at least one chemical substance of claim 4, wherein said system is included in a law enforcement protocol.

14. The method for verifying the composition of at least one chemical substance of claim 4, wherein said at least one chemical substance is at least one of a drug, a medication, a compounded medication, a compounded chemical formulation, a controlled substance, a narcotic, an illegal drug, an alcohol a food product and a perfume.

\* \* \* \* \*